(12) United States Patent
Soukup et al.

(10) Patent No.: US 7,015,353 B2
(45) Date of Patent: Mar. 21, 2006

(54) PROCESS FOR THE PRODUCTION OF 9-(Z)-RETINOIC ACID

(75) Inventors: Milan Soukup, Bottmingen (CH); Rolf Thomessen, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/819,693

(22) Filed: Apr. 7, 2004

(65) Prior Publication Data

US 2004/0235951 A1 Nov. 25, 2004

(30) Foreign Application Priority Data

Apr. 11, 2003 (EP) ................................. 03008020

(51) Int. Cl.
*C07D 61/22* (2006.01)
(52) U.S. Cl. .................................................. 562/510
(58) Field of Classification Search ................ 562/510
See application file for complete search history.

(56) References Cited

U.S. PATENT DOCUMENTS 5,504,230 A    4/1996    John et al.

FOREIGN PATENT DOCUMENTS

| DE | 1068710 | 11/1959 |
| EP | 0659739 | 12/1994 |
| WO | WO 99/09969 | 3/1999 |

OTHER PUBLICATIONS

Rüegg, et al., Helv. 44 985 (1961).

*Primary Examiner*—Rita Desai
(74) *Attorney, Agent, or Firm*—George W. Johnston; Dennis P. Tramaloni; Samuel H. Megerditchian

(57) ABSTRACT

A process for the production of 9-(Z)-retinoic acid is described which comprises reacting an alkali metal salt of 3-methyl-4-oxocrotonic acid with a $C_{15}$-triphenyl-phosphonium salt. 9-(Z)-retinoic acid is used in the treatment of dermatological diseases.

13 Claims, No Drawings

PROCESS FOR THE PRODUCTION OF 9-(Z)-RETINOIC ACID

BACKGROUND OF THE INVENTION 9-(Z)-RA is a versatile compound which is claimed to be useful for the treatment of numerous dermatological diseases as e.g. disclosed in WO 99/09969.

The EP-A 0 659739 discloses a process for the preparation of 9-(Z)-RA which is characterized by the Wittig-reaction of an alkyl β-formylcrotonate with a $C_{15}$-triarylphosphonium salt in the presence of a base and by the subsequent saponification of the so formed retinoic acid ester with a base.

This process suffers from the disadvantage that it requires two steps involving a change of solvent for the saponification of the retinoic acid ester. Since the saponifaction needs quite drastic temperature conditions a significant formation of unwanted isomers has also been observed.

SUMMARY OF THE INVENTION

The present invention provides a process for the preparation of 9-(Z)-retinoic acid, comprising reacting an alkali metal salt of 3-methyl-4-oxocrotonic acid of the formula

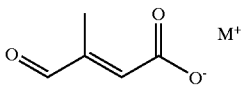

I wherein M stands for sodium or potassium, with the (Z)-isomer of a $C_{15}$-triphenyl phosphonium salt of the formula

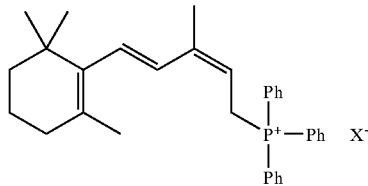

II wherein X stands for a halogen, in the presence of a base.

DETAILED DESCRIPTION OF THE INVENTION

The present invention provides a process which is characterized by the reaction of an alkali metal salt of 3-methyl-4-oxocrotonic acid of the formula

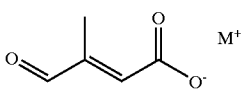

I wherein M stands for sodium or potassium, with the (Z)-isomer of a $C_{15}$-triphenyl phosphonium salt of the formula wherein Ph stands for phenyl and X stands for a halogen, in the presence of a base.

The alkali metal salt of methyl-4-oxocrotonic acid is, in a preferred embodiment, prepared in situ from an alkyl-3-methyl-4-oxocrotonate which is hydrolyzed in the presence of an alkali hydroxide, and without isolation it is used for the subsequent reaction step.

However, the alkali metal of methyl-4-oxocrotonic acid can of course also be isolated before using it for the reaction with the (Z)-isomer of a $C_{15}$-triphenyl phosphonium salt of formula II.

Most preferably the potassium salt of methyl-4-oxocrotonic acid is prepared from ethyl-3-methyl-4-oxocrotonate by hydrolysis with potassium hydroxide.

It has been found that the hydrolysis is preferably performed in the presence of a lower alcohol, most preferably in ethanol at temperatures between −10° C. and 10° C., ideally between 0° C. and 5° C. The preferred potassium hydroxide is conveniently applied in the form of an aqueous solution, e.g. of 50%.

The (Z)-isomer of the $C_{15}$-triphenyl phosphonium salt occurs in the form of an isomeric mixture together with the (E)-isomer in a mother liquor which is obtained in the preparation of β-carotene. (Rüegg et al., Helv. 44, 985 (1961)).

This mother liquors as a rule contains both the (Z)- and the (E)-isomer in a ratio which may vary but as a rule is about 2:1.

The (Z)-isomer of the $C_{15}$-triphenyl phosphonium salt can in a preferred embodiment of the invention be isolated from this mother liquor according to the following steps:
a) extraction of a concentrate of the mother liquor with methylene chloride,
b) taking up of the organic phase in ethylacetate/n-butanol,
c) distilling off ethylacetate/methylene chloride,
d) replacing the distilled amount by ethylactetate,
e) crystallizing out the (Z)-isomer, and
f) filtering and drying.

It has been found that in step b) the n-butanol content in the ethylacetate is advantageously chosen in the range of 3% to 10%, preferably 3% to 5%.

It may be necessary that crystallization has to be initiated by seeding with crystals of 9-(Z)-RA.

Preferred $C_{15}$-triphenyl phosphonium salt of formula II is the chloride salt. Delivery of the (Z)-isomer for the subsequent conversion into the 9-(Z)-RA advantageously takes place in the form of an alcoholic solution, most preferably in the form of an ethanolic solution.

The process is expediently performed at a temperature from −15° C. to 15° C., preferably at a temperature between 0° C. and 5° C. Temperatures outside this range either lead to a slowdown of the reaction or to an increased by-product formation.

Advantageously the reaction is performed in the presence of a lower alcohol, preferably in ethanol.

Suitable base for the conversion into the 9-(Z)-RA is an alkali hydroxide. Preferably sodium hydroxide or potassium hydroxide, most preferably potassium hydroxide in the form of an aqueous solution of e.g. 50% is used.

The work up of the reaction mixture can take place by the following steps:
a) extraction with an organic solvent, preferably with methylene chloride,
b) setting the pH of the water phase to about 3 to 4 with a suitable mineral acid e.g. with phosphoric acid,
c) extraction with methylene chloride,
d) exchange of solvent towards methanol by distilling off methylene chloride and, preferably at the same time, continuous introduction of methanol,
e) separation of the 9-(Z)-RA which crystallizes from the mixture.

Further purification of 9-(Z)-RA can be achieved by a recrystallization in a lower alcohol, preferably in isopropanol.

With regard to the sensitivity of the reactants and of the product it is crucial that the reaction steps are performed largely under the exclusion of light and oxygen.

The following examples shall illustrate the invention without limiting it.

EXAMPLES

Example 1 a) Isolation of 9-(Z)-$C_{15}$-triphenylphosphoniumchloride 200, 0 g of an oily concentrate containing an isomeric mixture of 9-(Z)- and 9-(E) $C_{15}$-triphenylphosphoniumchloride (E-content 18%, Z-content content 36%) was taken up and mixed with 400 ml of methylene chloride under an argon atmosphere at 20 to 25° C. The water phase was separated, and then 1000 ml ethylacetate were added in the course of 5 to 10 minutes at 15 to 25° C. 35 ml n-butanol was then added to the clear orange-brown solution previously obtained. The ethylacetate and methylene chloride was distilled off at 28 to 33° C./180 to 200 mbar, whereby the amount which was distilled off was replaced with 1600 ml of ethylacetate. Crystallization of the 9-(Z)-$C_{15}$-triphenylphosphoniumchloride was initiated with 0.2 ml of a suspension of 9-(Z)-$C_{15}$-triphenylphosphoniumchloride at 30 to 35° C. The suspension was then stirred for another 2 to 3 hours at 30 to 35° C. The crystals were then filtered, washed with 400 ml of ethylacetate and then dried under vacuum at 40° C./25 mbar. 62.06 g (31.0% based on the oily concentrate) of 9-(Z)-$C_{15}$-triphenylphosphoniumchloride (content 93.6% Z-isomer (HPLC)) in the form of white crystals were obtained.

b) Preparation of 9-(Z)-Retinoic Acid

In an argon atmosphere 40.4 g (278.5 mmol) ethyl-3-methyl-4-oxocrotonate were taken up in 80 ml of ethanol. 30.6 g (272.7 mmol) of a 50% aqueous solution of potassium hydroxide was then carefully added in the course of 20 minutes thereby keeping the reaction temperature at 0 to 5° C. The mixture was then stirred at this temperature until the ester disappeared in the HPLC chromatograph. Thereafter 258.0 g of an ethanolic solution of 9-(Z)-$C_{15}$-triphenylphosphoniumchloride (content 38.8%, 199.5 mmol) was carefully added in the course of 20 minutes. During the addition the reaction temperature was kept at 0 to 5° C. Then 29.8 g (265.6 mmol) of a 50% aqueous solution of potassium hydroxide was then carefully added in the course of 20 minutes thereby keeping the reaction temperature at 0 to 5° C. The mixture was then stirred at this temperature until the phosphonium salt disappeared in the HPLC chromatograph. To the orange suspension so formed 900 ml deionized water were added whereby a clear orange solution was formed. The mixture was stirred for another 10 minutes, then 400 ml of deionized water and 260 ml methylene chloride were added and stirred for another 10 minutes. The organic phase was separated; the water phase then was three times extracted with a total volume of 540 ml methylene chloride. The organic phase was separated. The water phase was adjusted to a pH of 3.5 to 4.0 with 21 ml of phosphoric acid 85% and stirred for 20 minutes at 20 to 30° C. under argon atmosphere. The water phase was then extracted with 200 ml methylene chloride and the water phase further extracted two times with a total of 160 ml of methylene chloride. The combined organic phase was filtered. An exchange of solvent towards methanol was achieved by distilling off methylene chloride starting at 30° C./250 mbar and ending at 40° C./700 mbar and by at the same time adding 800 ml methanol. 9-(Z)-retinoic acid starts to crystallize out in the course of the distillation. The suspension was then cooled down to 0 to 5° C. and stirred for 2 hours. The yellow-orange suspension was filtered, washed with a total of 170 ml of methanol of 0 to 5° C. and the so obtained crystals were dried in the vacuum at 40 to 50° C./30 mbar overnight. 10.6 g (17.7%) of the product was obtained in the form of yellow crystals and with a content of 98.5%.

c) Crystallization of 9-(Z)-Retinoic Acid

Under argon atmosphere 28.0 g 9-(Z)-retinoic acid were taken up in 1120 ml of isopropanol at about 20° C. The suspension was heated to 60 to 70° C., whereby a clear yellow solution was formed. Crystallization occurred by slowly cooling down to 0 to 5° C. The suspension was then filtered and washed with cold isopropanol and the so obtained crystals were dried in the vacuum at 40 to 50° C./30 mbar overnight. 24.4 g (87.3%) of analytically pure 9-(Z)-retinoic acid was obtained in the form of yellow crystals.

What is claimed is:

1. A process for the preparation of 9-(Z)-retinoic acid, comprising reacting an alkali metal salt of 3-methyl-4-oxocrotonic acid of the formula

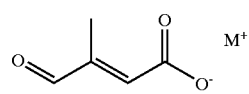

wherein M stands for sodium or potassium, with the (Z)-isomer of a $C_{15}$-triphenyl phosphonium salt of the formula

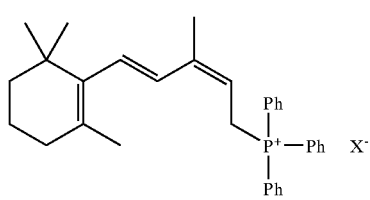

wherein X stands for a halogen, in the presence of a base.

2. The process according to claim 1, wherein the alkali metal salt of methyl-4-oxocrotonic acid is prepared in situ from an alkyl-3-methyl-4-oxocrotonate which is hydrolyzed in the presence of an alkali hydroxide.

3. The process according to claim 2, wherein M stands for potassium, and the potassium salt of methyl-4-oxocrotonic acid is prepared in situ from ethyl-3-methyl-4-oxocrotonate which is hydrolyzed in the presence of potassium hydroxide.

4. The process according to claim 1, wherein $X^-$ in formula II is chlorine.

5. The process according to claim 1, wherein the (Z)-isomer of a $C_{15}$-triphenyl phosphonium salt is isolated from an isomeric mixture of the (Z)-isomer and the (E)-isomer, comprising the steps:
   a) extracting a concentrate of the isomeric mixture with methylene chloride,
   b) taking up the organic phase in ethylacetate/n-butanol,
   c) distilling off ethylacetate/methylene chloride,
   d) replacing the distilled amount with ethylactetate, and
   e) crystallizing out the (Z)-isomer.

6. The process according to claim 1, wherein the reaction is performed at a temperature of from −15° C. to 15° C.

7. The process according to claim 1, wherein the reaction is performed in the presence of a lower alcohol.

8. The process according to claim 1, wherein the base is an alkali hydroxide.

9. The process according to claim 8, wherein the base is potassium hydroxide.

10. The process according to claim 1, wherein the process further comprises:
   a) extracting the alkali metal salt of 3-methyl-4-oxocrotonic acid and (Z)-isomer of a $C_{15}$-triphenyl phosphonium salt mixture with methylene chloride,
   b) setting the pH of the water phase to about 3 to 4 with a mineral acid,
   c) extracting with methylene chloride,
   d) exchanging solvent with methanol by distilling off methylene chloride and introducing methanol, and
   e) isolating the 9-(Z)-retinoic acid which crystallizes from the mixture.

11. The process according to claim 5, wherein the isomeric mixture is comprised in a mother liquor obtained from the preparation of β-carotene, and the ratio of the (Z) to the (E) isomer in the mixture is about 2:1.

12. The process according to claim 1, wherein the reaction temperature is from −15° C. to 15° C.

13. The process according to claim 1, wherein the reaction occurs substantially free from the presence of light and oxygen.

* * * * *